United States Patent [19]

Papas et al.

[11] Patent Number: 5,593,682

[45] Date of Patent: Jan. 14, 1997

[54] SKIN TREATING COMPOSITION

[75] Inventors: Andreas M. Papas; Howard K. Hobbs, both of Kingsport, Tenn.

[73] Assignee: Eastman Chemical Company, Kingsport, Tenn.

[21] Appl. No.: 580,870

[22] Filed: Dec. 29, 1995

[51] Int. Cl.$^6$ .................................................. A61K 7/48
[52] U.S. Cl. ............................................... 424/401
[58] Field of Search .............................................. 424/401

[56] References Cited

U.S. PATENT DOCUMENTS 5,447,729  9/1995  Belenduik et al. ..................... 424/490

*Primary Examiner*—Amy Hulina
*Attorney, Agent, or Firm*—Harry J. Gwinnell; John D. Thallemer

[57] ABSTRACT

The present invention relates to a skin treating composition containing vitamin E; a blend comprising acetylated monoglyceride and polyoxyethylene fatty acid ester; a blend comprising distilled monoglyceride, distilled propylene glycol monoester, and sodium or calcium stearoyl lactylate; water; and oxidized cellulose. The skin treating composition reduces inflammation, swelling, and itching, and reduces formation of scars in the tissue.

1 Claim, No Drawings

SKIN TREATING COMPOSITION

FIELD OF THE INVENTION

The present invention relates to a skin treating composition containing vitamin E; a blend comprising acetylated monoglyceride and polyoxyethylene fatty acid ester; a blend comprising distilled monoglyceride, distilled propylene glycol monoester, and sodium or calcium stearoyl lactylate; water; and oxidized cellulose.

BACKGROUND OF THE INVENTION

Since increased moisture content is believed to be responsible for increasing the flexibility of the skin, the application of oils, water in oil or oil in water emulsions to the skin so as to form a barrier which reduces the escape of moisture from the skin is an important characteristic of cosmetics.

The hydrocarbons such as petrolatum, mineral oil, paraffin wax and ozokerite, as well as many other emollient materials have long been used in skin creams and lotions. These materials function as emollients by covering the skin with a hydrophobic occlusive film which prevents water loss from the skin surface to the environment. In addition, animal fats and oils such as lanolin and its various derivatives such as acetylated lanolins, have been used in many skin creams and lotions as the emollient of choice, depositing on the skin, films that are hydrophobic, waxy, protective and emollient in character.

While the foregoing emollient materials have valuable moisturizing and skin softening properties when utilized in skin creams and lotions, they also possess undesirable effects in that they lack good tactile properties and generally impart to the skin as uncomfortable feeling of warmth in addition to a sticky, oily, greasy or waxy feel. These materials have little effect, if any, on reducing inflammation, swelling and itching and scarring of tissue.

There is therefore a continuing need for the development of new and improved skin treating compositions which impart beneficial effects to the skin, especially in alleviating inflammation, itching and scarring associated with dermatitis, burns and injury.

Example of current hemorrhoid treating composition is Preparation H$^R$ containing live yeast cell derivative and shark liver oil. Hydrocortisone preparations are used for relieving swelling and itching. Corticosteroids in general are used for treatment of several forms of dermatitis. While corticosteroids are very effective in reducing swelling and itching, with prolonged use they have major serious side effects. These include fluid and electrolyte disturbances, impaired wound healing and musculoskeletal, gastrointestinal, neurological, endocrine and other disturbances. One major weakness of corticosteroid products is that they impair instead of promoting wound healing associated with some of these skin conditions. In addition, they have no beneficial effect in reducing scarring.

SUMMARY OF THE INVENTION

The present invention relates to skin treating compositions comprising:

(A) 1 to 25 weight percent of vitamin E;

(B) 1 to 20 weight percent of a blend comprising acetylated monoglyceride and polyoxyethylene fatty acid ester;

(C) 1 to 30 weight percent of a blend comprising distilled monoglyceride, distilled propylene glycol monoester, and sodium or calcium stearoyl lactylate; and (D) 25 to 95 weight percent water, wherein the weight percents are based on the total skin treating composition.

DESCRIPTION OF THE INVENTION

The skin treatment compositions of the present invention may be applied to the skin, i.e., the arms, the legs, the entire body, where treatment and/or conditioning is desired, by smoothing it over the skin. The skin treating compositions, when applied to the skin, provide thin, substantive, flexible films which do not crack, peel or flake; are water-proof or highly resistant to water; do not have an oily, greasy, sticky or waxy feel and provide good, long-term adhesion of cosmetically active materials to the skin; and, in appropriate circumstances, reduce inflammation, swelling, and itching, promote wound healing, and reduce scarring.

The first component, component (A), of the skin treating composition is vitamin E. As used herein, the term "vitamin E" refers to α, β, γ, and δ-tocopherol. The vitamin E may also be a combination of α, β, γ, and δ-tocopherols. The α-form occurs naturally as the d-isomer known as d-α-tocopherol (d-2,5,7,8-tetramethyl-2-(4',8'12'-trimethyltridecyl)-6-chromanol). Other forms of vitamin E which can be used include: d-α-tocopheryl acetate, d-α-tocopheryl succinate, d-α-tocopheryl nicotinate and d-α-tocopheryl linoleate. Also the corresponding dl forms may be used which include: dl-α-tocopherol, dl-α-tocopheryl acetate, dl-α-tocopheryl succinate, dl-α-tocopheryl nicotinate and dl-α-tocopheryl linoleate.

An especially preferred combination of vitamin E is d-α-tocopheryl acetate and d-α-tocopheryl polyethylene glycol 1000 succinate (TPGS, a water-soluble vitamin E form with surfactant activity). Vitamin E TPGS is commercially available from Eastman Chemical Company. The vitamin E is present in an amount ranging from 1 to 25 weight percent, preferably 5 to 20 weight percent of the total skin treating composition.

The second component, component (B), of the skin treating composition is a blend comprising acetylated monoglyceride and a polyoxyethylene fatty acid ester. Component (B) is present in an amount of 1 to 20 weight percent, preferably 3 to 10 weight percent, based on the total skin treating composition. The acetylated monoglyceride may be either mono or di acetylated or a mixture thereof. The acetylated monoglyceride serves as a solvent for vitamin E and other materials in the skin treating composition. The acetylated monoglyceride acts also as an emollient and occlusive.

Acetylated monoglycerides are modified fats produced by the interesterification and subsequent molecular distillation of triglycerides, triacetin, and glycerin. More than one acetylated monoglyceride may be used in the skin treating compositions. Preferred acetylated monoglycerides are available under the trademark MYVACET Distilled Acetylated Monoglycerides from Eastman Chemical Company. Specific examples of MYVACET Distilled Acetylated Monoglycerides are: MYVACET 5-07, 7-07, 9-08, and 9-45. MYVACET 5-07 is prepared from hydrogenated vegetable oil, and has a hydroxyl value of 133–152, a saponification value of 279–292, an acetylation % of 48.5–51.5, an iodine value of 5 or less, a melting point of 41°–46° C., and is in the form of a waxy solid. MYVACET 7-07 is prepared from hydrogenated vegetable oil, and has a hydroxyl value of 80.5–95, a saponification value of 316–331, an acetylation % of 66.5–69.5, an iodine value of 5 or less, a melting point of 37°–40° C. and is in the form of a waxy solid. MYVACET 9-08 is prepared from hydrogenated coconut oil, and has a hydroxyl value of 20 max., a saponification value of 440–445, an acetylation % of 96 min., an iodine value of 2 or less, a melting point of −12° C. to −14° C., and is in the form of a liquid. MYVACET 9-45 is prepared from partially hydrogenated soybean oil, and has a hydroxyl value of 0–15, a saponification value of 370–382, an acetylation % of 96 min., an iodine value of 43–53, a melting point of 4° C. to 12° C., and is in the form of a liquid.

The polyoxyethylene fatty acid ester is commonly known as a polysorbate which is obtained by esterification of sorbitol with one or three molecules of a fatty acid such as stearic, lauric, oleic, and palmitic acid, under conditions which cause splitting out of water from the sorbitol, leaving sorbitan. Preferably the polyoxyethylene fatty acid ester is selected from polysorbate 20 (polyoxyethylene (20) sorbitan monolaurate), polysorbate 60 (polyoxyethylene (20) sorbitan monostearate), polysorbate 80 (polyoxyethylene (20) sorbitan monooleate), and polysorbate 65 (polyoxyethylene (20) sorbitan tristearate). While the ratio of acetylated monoglyceride and polyoxyethylene fatty acid ester in the blend may vary, preferably the acetylated monoglyceride and polyoxyethylene fatty acid ester are present in about a 1:1 ratio.

The third component, component (C), of the skin treating composition is a blend comprising distilled monoglyceride, distilled propylene glycol monoester, and sodium or calcium stearoyl lactylate. Component (C) is present in an amount of 1 to 30 weight percent, preferably 3 to 10 weight percent, based on the total skin treating composition. A preferred blend is available as TEXTURE LITE food emulsifier from Eastman Chemical Company. TEXTURE LITE is prepared from distilled monoglycerides having soybean oil as the fat source, distilled propylene glycol monoester, sodium stearoyl lactylate with silicon dioxide, and is in the form of a powder.

The distilled monoglyceride is a glycerol ester of fatty acids in which only one acid is attached to the glycerol group. The distilled monoglyceride may be unsaturated or saturated and is present in an amount of 20 to 80 weight percent, preferably 37 weight percent, of the component (C) blend. A preferred distilled monoglyceride is MYVEROL 18-06 available from Eastman Chemical Company which is prepared from hydrogenated soybean oil and has a minimum monoester content of 90%.

The distilled propylene glycol monoester is prepared by interesterification of propylene glycol with vegetable oil such as soybean oil followed by molecular distillation. The distilled propylene glycol monoester is present in an amount of 20 to 80 weight percent, preferably 51 weight percent, of the component (C) blend. A preferred distilled propylene glycol monoester is MYVEROL P-06 available from Eastman Chemical Company which is prepared from hydrogenated soybean oil and has a minimum monoester content of 90%. The sodium or calcium stearoyl lactylate is present in an amount of 5 to 20 weight percent, preferably 12 weight percent, of the component (C) blend.

The fourth component, component (D), of the skin treating composition is water. Water may be distilled or tap water. Distilled water is preferred because it is free of metals and odors.

Optionally, the skin treating compositions of the present invention may contain oxidized cellulose, component (E).

Oxidized cellulose refers to cellulose specifically oxidized and containing aldehyde or carboxy groups. The preferred form of oxidized cellulose contains a carboxy group in the $C_6$ carbon. Oxidized cellulose is available from Eastman Chemical Company.

Oxidized cellulose has hemostatic properties and aids in stopping bleeding. It is particularly beneficial when conditions such as hemorrhoids or excessive scratching in response to itching or inflammation causes bleeding. In addition, oxidized cellulose may be degraded by enzymes of the carbohydrase system and thus it is biodegradable and part of it may be absorbed in the tissue without adverse effects. The incorporation of oxidized cellulose in skin lesions resulting from the above and other conditions, not only does not hinder healing but it is helpful in absorbing fluids and aids healing. The combination of oxidized cellulose and vitamin E, is particularly effective in helping directly to stop bleeding, and indirectly aids healing by reducing and inflammation, itching and the severity of scars. The preferred range of oxidized cellulose in the composition is 1–4% weight percent based on the total skin treating composition. In cases where only itching is involved without bleeding or risk of skin damage due to excessive scratching, oxidized cellulose may be omitted from the preparation.

The skin treating compositions of the present invention when applied to the skin, provide thin, substantive, flexible films which do not crack, peel or flake; are water-proof or highly resistant to water; do not have an oily, greasy, sticky or waxy feel and provide good, long-term adhesion of cosmetically active materials to the skin; and, in appropriate circumstances, reduce inflammation, swelling, and itching, and promote wound healing.

Optionally, the skin treating compositions of the present invention may include plasticizing agents, opacifiers, surfactants, fragrances, sunscreens, antifungals, antibiotics, insect repellents, preservatives, emollients, humectants, emulsifiers, thickeners, moisturizers, astringents, deodorants, as well as other compatible materials which may be desired to enhance the cosmetic properties of the compositions. The optional cosmetic ingredients may be present in widely varying amounts depending upon the particular ingredients selected and the results desired. The skin treating compositions may additionally be combined with cortisteroids and/or antimicrobials.

The emollient materials are selected from among the hydrocarbon oils and waxes, as well as fatty acid esters such as butyl stearate, isopropyl stearate, isopropyl palmitate, isopropyl myristate and volatile silicone fluids composed of low molecular weight dimethyl siloxanes that have been assigned CTFA name cyclomethicone and are exemplified by Volatile Silicone 7207, a trademarked product of Union Carbide Corporation and the following trademarked product of Dow Corning Corporation: Dow Corning 244 Fluid and Dow Corning 245 Fluid.

The skin treating compositions of the present invention may be formulated by simply mixing all of the components at a temperature of 140° F. to 200° F. Preferably, the skin treating compositions are prepared at a temperature of 160° F. to 180° F., more preferably 170° F. If water is to be added to the skin treating composition, then the water is preferably added prior to adding the oxidized cellulose.

The skin treating compositions of the present invention find utility in topical application to reduce symptoms of skin inflammation, swelling and itching associated with hemorrhoids, dermatitis and burns. Additional uses include acne, antifungal, poison ivy, poison oak, poison sumac, diaper rash, insect bite, analgesic, anesthetic, antipruritic, moisturizers, astringents, antibiotic, make-up, deodorant, antiperspirant, hair dye and other lotions and creams designed for topical application.

The following examples are intended to illustrate, but not limit, the scope of this invention. All parts and percentages in the examples are on a weight basis unless otherwise stated.

EXAMPLE 1

A skin treating composition was prepared which contained:
I. heating to form a molten mixture

| | |
|---|---|
| d-α-tocopheryl acetate (Eastman Vitamin E 6-81) | 20% |
| Vitamin E TPGS | 0.2% |
| Blend 50/50 of MYVACET 9-45 Distilled Acetylated Monoglyceride and Polysorbate 60 | 5% |
| Oxidized cellulose | 4% |
| MYVATEX TEXTURE LITE | 6% |

II. mixing the molten mixture formed in Step I with

| | |
|---|---|
| Potassium Sorbate | 0.6% |
| Deionized water | 64.2% |

III. cooling the mixture of Step II while continually mixing to form a skin treating composition.

EXAMPLE 2

A skin treating composition was prepared which contained:
I. heating to form a molten mixture

| | |
|---|---|
| d-α-tocopheryl acetate (Eastman Vitamin E 6-81) | 20% |
| Vitamin E TPGS | 0.2% |
| Blend 50/50 of MYVACET 9-45 Distilled Acetylated Monoglyceride and Polysorbate 60 | 5% |
| Oxidized cellulose | 4% |
| 4-chloro-3,5 dimethyl phenol 99% | 1% |
| MYVATEX TEXTURE LITE | 6% |

II. mixing the molten mixture formed in Step I with

| | |
|---|---|
| Potassium Sorbate | 0.6% |
| Deionized water | 63.2% |

III. cooling the mixture of Step II while continually mixing to form a skin treating composition.

EXAMPLE 3

A skin treating composition was prepared which contained:
I. heating to form a molten mixture

| | |
|---|---|
| d-α-tocopherol | 20% |
| Vitamin E TPGS | 0.2% |
| Blend 50/50 of MYVACET 9-45 Distilled Acetylated Monoglyceride and Polysorbate 60 | 5% |
| Oxidized cellulose | 4% |
| MYVATEX TEXTURE LITE | 6% |

II. mixing the molten mixture formed in Step I with

| | |
|---|---|
| Potassium Sorbate | 0.6% |
| Deionized water | 64.2% |

III. cooling the mixture of Step II while continually mixing to form a skin treating composition.

EXAMPLE 4

A skin treating composition was prepared which contained:
I. heating to form a molten mixture

| | |
|---|---|
| d-α-tocopherol (Eastman vitamin E 5-67) | 20% |
| Vitamin E TPGS | 0.2% |
| Blend 50/50 of MYVACET 9-45 Distilled Acetylated Monoglyceride and Polysorbate 60 | 5% |
| Oxidized cellulose | 4% |
| 4-chloro-3,5 dimethyl phenol 99% | 1% |
| MYVATEX Texture Lite | 6% |

II. mixing the molten mixture formed in Step I with

| | |
|---|---|
| Potassium Sorbate | 0.6% |
| Deionized water | 63.2% |

III. cooling the mixture of Step II while continually mixing to form a skin treating composition.

EXAMPLE 5

The skin treatment composition according to Example 1 was prepared except that 0.5% hydrocortisone was added to replace an equivalent amount of water.

EXAMPLE 6

The skin treatment composition according to Example 2 was prepared except that 0.5% hydrocortisone was added to replace an equivalent amount of water.

EXAMPLE 7

The skin treatment composition according to Example 3 was prepared except that 1.0% hydrocortisone was added to replace an equivalent amount of water.

EXAMPLE 8

The skin treatment composition according to Example 4 was prepared except that 1.0% hydrocortisone was added to replace an equivalent amount of water.

EXAMPLE 9

A skin treating composition was prepared which contained:
I. heating to form a molten mixture

| | |
|---|---|
| d-α-tocopheryl acetate (Eastman Vitamin E 6-100) | 20% |
| Blend 50/50 of MYVACET 9-45 Distilled Acetylated Monoglyceride and Polysorbate 60 | 5% |
| MYVATEX TEXTURE LITE | 6% |

II. mixing the molten mixture formed in Step I with

| | |
|---|---|
| Vitamin E TPGS | 0.2% |
| Potassium sorbate | 0.6% |
| Deionized water | 68.2% |

III. cooling the mixture of Step II while continually mixing to form a skin treating composition.

EXAMPLE 10

A skin treating composition was prepared which contained:
I. heating to form a molten mixture

| | |
|---|---|
| d-α-tocopheryl acetate (Eastman Vitamin E 6-100) | 20% |
| Blend 50/50 of MYVACET 9-45 Distilled Acetylated Monoglyceride and Polysorbate 60 | 5% |
| MYVATEX TEXTURE LITE | 6% |

II. mixing the molten mixture formed in Step I with

| | |
|---|---|
| Vitamin E TPGS | 0.2% |
| Oxidized Cellulose | 4% |
| Potassium sorbate | 0.6% |
| Deionized water | 64.2% |

III. cooling the mixture of Step II while continually mixing to form a skin treating composition.

EXAMPLE 11

The skin treatment composition according to Example 9 was prepared except that 0.5% hydrocortisone was added to replace an equivalent amount of water.

EXAMPLE 12

The skin treatment composition according to Example 10 was prepared except that 0.5% hydrocortisone was added to replace an equivalent amount of water.

EXAMPLE 13

Skin Treating Composition Used as Hemorrhoid Treatment.

The skin treating composition prepared in Example 1 was applied to the anal area of a man who was experiencing inflammation of the anal area, swelling and pruritus anus. The inflammation, burning and swelling subsided within an hour after application of the skin treating composition. Another application of the skin treating composition was made after 24 and 48 hours, respectively. Following the two additional applications of the skin treating composition, the symptoms essentially disappeared.

EXAMPLE 14

Skin Treating Composition Used to Treat Contact Dermatitis.

The skin treating composition prepared in Example 1 was applied to the skin of a man experiencing contact dermatitis characterized by inflammation, vesicles, oozing, crusting, severe itching, and minor bleeding. The inflammation, burning, itching and bleeding subsided within three hours after application of the skin treating composition. Another application of the skin treating composition was made twice a day for five days wherein the symptoms were eliminated and no scarring remained.

EXAMPLE 15

Skin Treating Composition Used to Treat Skin Carcinomas.

The skin treating composition prepared in Example 5 was applied to the skin of a woman, age 82, who had areas of skin with darker pigmentation especially on the face. Due to his genetic predisposition and extensive exposure to sunlight, several of the spots had developed into ulcer-type wounds and skin carcinomas. The spots had previously been treated by radiation, however, the spots continued to redevelop into ulcer-type wounds with itching and occasional bleeding and scarring. Application of the skin treating composition provided relief of itching for hours and reduced bleeding and scarring.

EXAMPLE 16

Skin Treating Composition Used to Treat Skin Carcinomas.

The skin treating composition prepared in Example 1 was applied to the skin of a man who was the son of the woman in Example 15. The son, like his mother, also had areas of skin with darker pigmentation especially on the face. Due to his genetic predisposition and extensive exposure to sunlight, several of the spots had been diagnosed as starting to develop into ulcer-type wounds and skin carcinomas.

Following application of the skin treating composition, the color of the spots became significantly lighter.

EXAMPLE 17

Skin Treating Composition Used to Treat Burns.

The skin treating composition prepared in Example 1 was applied to the skin of a man who suffered burn-type symptoms (reddish sensitive skin and itching) from overexposure in a tanning booth. The burning and itching subsided within one hour after a single application of the skin treating composition.

Many variations will suggest themselves to those skilled in this art in light of the above detailed description. All such obvious modifications are within the full intended scope of the appended claims.

What is claimed is:

1. A skin treating composition comprising:
   (A) 1 to 25 weight percent of vitamin E;
   (B) 1 to 20 weight percent of a blend comprising acetylated monoglyceride and polyoxyethylene fatty acid ester;
   (C) 1 to 30 weight percent of a blend comprising distilled monoglyceride, distilled propylene glycol monoester, and sodium or calcium stearoyl lactylate;
   (D) 25 to 95 weight percent water;
   (E) 0.1 to 10 weight percent of oxidized cellulose, wherein the weight percents are based on the total skin treating composition.

* * * * *